US008815312B2

(12) United States Patent
Falk et al.

(10) Patent No.: US 8,815,312 B2
(45) Date of Patent: Aug. 26, 2014

(54) METHODS OF USE AND NUTRITIONAL COMPOSITIONS OF TOUCHI EXTRACT

(75) Inventors: Anne Falk, Salt Lake City, UT (US); Zamzam (Fariba) Roughead, Plymouth, MN (US); Kevin Burke Miller, Minneapolis, MN (US); Satya Jonnalagadda, Plymouth, MN (US); Norman Alan Greenberg, New Hope, MN (US); Kala Marie Kaspar, St. Louis Park, MN (US); Julie Swanson, Minneapolis, MN (US)

(73) Assignee: Nestec S.A., Vevey (CH)

( * ) Notice: Subject to any disclaimer, the term of this patent is extended or adjusted under 35 U.S.C. 154(b) by 471 days.

(21) Appl. No.: 12/300,426

(22) PCT Filed: May 24, 2007

(86) PCT No.: PCT/US2007/069624
§ 371 (c)(1),
(2), (4) Date: Jan. 20, 2009

(87) PCT Pub. No.: WO2007/140230
PCT Pub. Date: Dec. 6, 2007

(65) Prior Publication Data
US 2009/0148545 A1 Jun. 11, 2009

Related U.S. Application Data

(60) Provisional application No. 60/803,244, filed on May 26, 2006.

(51) Int. Cl.
*A61K 36/48* (2006.01)
*A23F 5/00* (2006.01)
*A61K 36/00* (2006.01)

(52) U.S. Cl.
USPC .............................. 424/757; 426/45; 424/725

(58) Field of Classification Search
None
See application file for complete search history.

(56) References Cited

U.S. PATENT DOCUMENTS

| | | | |
|---|---|---|---|
| 6,080,401 A * | 6/2000 | Reddy et al. | 424/93.3 |
| 7,108,869 B2 | 9/2006 | Murray et al. | |
| 2002/0187219 A1 | 12/2002 | Yang et al. | |
| 2004/0037868 A1 * | 2/2004 | Minich et al. | 424/439 |
| 2004/0071680 A1 * | 4/2004 | Song et al. | 424/93.45 |
| 2004/0091554 A1 * | 5/2004 | Murray et al. | 424/725 |
| 2005/0277657 A1 * | 12/2005 | Ninkov | 514/263.31 |
| 2006/0051435 A1 * | 3/2006 | Udell et al. | 424/725 |
| 2007/0128178 A1 | 6/2007 | Corthesy-Theulaz et al. | |
| 2008/0075805 A1 | 3/2008 | Dorr et al. | |
| 2008/0193603 A1 | 8/2008 | Hayes et al. | |

FOREIGN PATENT DOCUMENTS

| | | |
|---|---|---|
| CN | 1686532 A * | 10/2005 |
| JP | 2000072687 | 3/2000 |
| JP | 2001010965 | 1/2001 |
| JP | 2003212783 | 7/2003 |
| JP | 2004154126 | 6/2004 |
| JP | 2004520065 | 7/2004 |
| JP | 2004323469 | 11/2004 |
| JP | 2005538087 | 12/2005 |
| JP | 2006513717 | 4/2006 |
| JP | 2006296251 | 11/2006 |
| JP | 2008506399 | 3/2008 |
| JP | 2008535840 | 9/2008 |
| RU | 2268069 | 3/2004 |
| WO | 2004 086881 | 10/2004 |
| WO | WO 2006/108008 | 10/2006 |

OTHER PUBLICATIONS

Fujita Hiroyuki et al, "Effect of Touchi extract on blood lipids in hypertriglyceridemic subjects and Sprague-Dawley rats", Nutrition Research, vol. 25, No. 7, Jul. 2005, pp. 681-692.
Fujita Hiroyuki et al, "Long-term ingestion of Touchi-extract, an alpha-glucosidase inhibitor, by borderline and mild type-2 diabetic subjects is safe and significantly reduces blood glucose levels,", Nutrition Research, vol. 23, No. 6, Jun. 2003, pp. 713-722.
Fujita Hiroyuki et al, "Fermented soybean-derived Touchi-extract with anti-diabetic effect via alpha-glucosidase inhibitory action in a long-term administration study with KKAy mice", Life Sciences, vol. 70, No. 2, Nov. 30, 2001, pp. 219-227.
Fujita Hiroyuki et al, "Long-term ingestion of a fermented soybean-derived Touchi-extract with alpha-glucosidase inhibitory activity is safe and effective in humans with borderline and mild type-2 diabetes", Journal of Nutrition, vol. 131, No. 8, Aug. 2001, pp. 2105-2108.
Hiroyuki Fujita et al, "Efficacy and safety of Touchi Extract, an alpha-glucosidase inhibitor derived from fermented soybeans, in non-insulin-dependent diabetic mellitus", Journal of Nutritional Biochemistry, vol. 12, No. 6, Jun. 2001, pp. 351-356.
Fujita Hiroyuki et al, "Fermented soybean-derived water-soluble Touchi extract inhibits alpha-glucosidase and is antiglycemic in rats and humans after single oral treatments", Journal of Nutrition, vol. 131, No. 4, Apr. 2001, pp. 1211-1213.

* cited by examiner

Primary Examiner — Qiuwen Mi
(74) Attorney, Agent, or Firm — K&L Gates LLP

(57) ABSTRACT

Disclosed is a method and composition for nutritional compositions containing glucosidase inhibitors, and more specifically Touchi Extract and its uses in the treatment of many disorders. These disorders include diabetes, hyperlipidemia, obesity, Metabolic syndrome/Syndrome X, COPD, malabsorption, Crohn's disease, diarrhea, constipation, irritable bowel syndrome, human immunodeficiency virus, cystic fibrosis, non-alcoholic steatohepatitis, polycystic ovarian syndrome including associate infertility, and erectile dysfunction. Further, glucosidase inhibitors, and more specifically Touchi Extract can be used to aid healing in critical care patients and for general wound healing. Additionally, glucosidase inhibitors, including Touchi Extract can be used to enhance athletic performance.

29 Claims, No Drawings

METHODS OF USE AND NUTRITIONAL COMPOSITIONS OF TOUCHI EXTRACT

CROSS REFERENCE TO RELATED APPLICATIONS

The present application is a National Stage of International Application No. PCT/US07/69624, filed on May 24, 2007, which claims priority to U.S. Provisional Application 60/803,244, filed May 26, 2006, the entire contents of which are being incorporated herein by reference.

TECHNICAL FIELD

The present invention relates generally to nutrition and more particularly to a method of use and nutritional compositions containing α-glucosidase inhibitors, and more specifically Touchi Extract.

BACKGROUND OF THE INVENTION

Touchi Extract (TE) is a water-extract powder of fermented soybeans. Touchi Extract is derived from soybeans that have been fermented with *Aspergillus Oryzae*. Touchi Extracthas been shown to inhibit α-glucosidase activity leading to lower blood glucose concentrations and HbA1c values in individuals with type 2 diabetes, similar to Acarbose and Voglibose. Touchi Extract inhibits α-glucosidase exclusively and does not inhibit other digestive enzymes like amylase, pepsin, trypsin, chymotrypsin or lipase.

In the past 25 years, US obesity rates have more than doubled. In 2000, the US prevalence of obesity was estimated to be 31%. The obesity epidemic is not limited to the US population. In the past 15 years, the prevalence of obesity among the majority of European populations has also increased 10 to 40%. Numerous studies have linked obesity with an increased risk of premature mortality, demonstrating that the probability of death increases as excess body weight increases. Obesity now accounts for approximately 112,000 deaths per year in the US, second only to tobacco use among preventable causes of death. It has been clearly demonstrated that weight loss alleviates symptoms and reduces the severity of many chronic conditions associated with obesity, including: hypertension, coronary heart disease, type 2 diabetes, osteoarthritis and sleep apnea. Moreover, weight loss prevents future illnesses by controlling underlying risk factors. Reducing body weight has been shown to protect against cardiovascular disease by lowering blood pressure, total cholesterol, low-density lipoprotein (LDL) cholesterol, and triglycerides Similarly, Metabolic Syndrome/Syndrome X is a cluster of metabolic risk factors, including elevated blood glucose, glucose intolerance, insulin resistance, elevated triglycerides, elevated LDL-cholesterol, low high-density lipoprotein (HDL) cholesterol, elevated blood pressure, abdominal obesity, pro-inflammatory states, and pro-thrombotic states. Individuals with metabolic syndrome are at increased risk of cardiovascular disease and coronary heart disease and other diseases related to plaquing of the artery walls and type 2 diabetes. Some of the risk factors of cardiovascular disease and coronary heart disease include impaired fasting glucose, elevated blood lipids (Total cholesterol, LDL-cholesterol, Triglycerides), low HDL-cholesterol, obesity, type 2 diabetes, elevated blood pressure, insulin resistance, and pro-inflammatory and pro-thrombotic factors.

SUMMARY OF THE INVENTION

The present invention relates to a method of use, composition or dietary regimen containing α-glucosidase inhibitors, and more specifically Touchi Extracts. Touchi Extract and other α-glucosidase inhibitors, as a result of their ability to inhibit carbohydrate breakdown, will act to increase the plasma concentration of glucagon-like peptide-1 (GLP-1) and glucagon-like peptide-2 (GLP-2).

GLP-1 acts to stimulate glucose-dependent insulin secretion, and pancreatic beta-cell proliferation and neogenesis. The increased plasma concentration of GLP-1 will improve glycemic control by stimulating insulin secretion in addition to the effect from Touchi Extract in delaying the appearance of glucose in the blood.

GLP-2 acts to enhance intestinal structure and function by improving crypt-villus architecture and increasing enzyme and transporter activities. The increased plasma concentration of GLP-2 will improve intestinal structure and function and reduce intestinal inflammation.

In addition, the combination of Touchi Extract and/or other α-glucosidase inhibitors with flavanols (i.e. epicatechin and catechin compounds from cocoa, wine, grape seed and green tea) may improve endothelial function by improving glycemic control and vasodilation.

Diabetes, starting from early insulin resistance, to late exogenous insulin dependence can be positively effected by Touchi Extract and/or other α-glucosidase inhibitors. Touchi Extract and/or other α-glucosidase inhibitors, inhibits the breakdown of carbohydrates, thus prolonging the time carbohydrates are present in the intestine and thereby delaying the post-prandial rise in blood glucose levels. This slower increase in post-prandial blood glucose concentrations can thus slow/delay the beta-cell secretion of insulin and thus minimize exposure of the body cells to high concentrations of insulin, thus contributing to improving insulin sensitivity and decreasing insulin resistance.

For obesity, Touchi Extract and/or other α-glucosidase inhibitors will act to improve glycemic control, improve satiety and delay gastric emptying further improving satiety in addition to the effect from Touchi Extract in delaying the appearance of glucose in the blood via actions of GLP-1.

In Metabolic Syndrome/Syndrome X, Touchi Extract and/or other α-glucosidase inhibitors, inhibit the breakdown of carbohydrates, thus prolonging the time carbohydrates are present in the intestine and thereby delaying the post-prandial rise in blood glucose concentrations thus mitigating some of the sequelae of this syndrome.

Another potential role of Touchi Extract and/or other α-glucosidase inhibitors is their ability to stimulate GLP-1, which in turn stimulates beta-cell insulin secretion and can thus help lower blood glucose concentrations, and contribute to lower blood lipids, inflammation and thrombotic factors, blood pressure and abdominal obesity.

Both insulin-resistance and chronic obstructive pulmonary disease (COPD) are linked to inflammatory conditions and oxidative stress. Providing Touchi Extract and/or other α-glucosidase inhibitors will benefit the individual through reduction of insulin secretion and hyperglycemia which lead to exacerbation of the condition.

The increased plasma concentration of GLP-2 from the Touchi Extract will help restore intestinal function in patients with malabsorption secondary to mucosal degeneration and will help optimize intestinal function including nutrient absorption in patients following bowel resection, including those with short-bowel syndrome and post-surgery for gastrointestinal malignancy and ulcerative colitis. Further, Touchi Extract will help restore normal intestinal function including the integrity of the gut barrier disrupted by intestinal inflammation.

The addition of probiotics and/or prebiotics can further improve the intestinal structure and function, and reduce inflammation as well as increase the immune response presented below.

In the case of commercially available sports products, excess blood sugar is stored for later use, a state which may actually cause hypoglycemia that could negatively impact athletic performance. Extending the period over which carbohydrates are metabolized to monosaccahrides for absorption through the use of Touchi Extract and/or other α-glucosidase inhibitors is thought to increase the endurance potential of athletes consuming the product.

The use of Touchi Extract will help manage aberrant glucose and lipid metabolism through its mechanism of slowing down glucose metabolism and absorption and, thus, decrease some of the complications associated with Human Immunodeficiency Virus.

Most patients with Cystic Fibrosis (CF) have obstruction of the pancreatic ducts, often leading to insufficient endocrine function, such as insufficient insulin availability. This insufficiency can lead to CF-related diabetes. The use of Touchi Extract to reduce post-prandial glucose excursions could be helpful in managing Cystic fibrosis-related diabetes.

Touchi Extract could be used to reduce post-prandial glucose excursions, therefore decrease insulin spikes and thus be helpful in managing the type 2 diabetes that is frequent in non-alcoholic steatohepatitis patients. In addition, Touchi Extract could be helpful in decreasing endogenous production of triglycerides, and therefore may play a role in helping manage the accumulation of fat in the liver, since the natural action of insulin is to lower the blood sugar concentration through entry of the glucose into the cells or by storage of the glucose, sometimes as fats, such as triglycerides.

The use of Touchi Extract in oral nutritional supplements (ONS) for critical care patients will improve glycemic control and reduce the risk of infections and other complications and improve the quality and rate of wound healing. The same rational for tube feedings containing Touchi Extract can be assumed.

Elevated blood glucose concentrations are known to delay wound healing. The use of Touchi Extract to reduce the post prandial glucose excursion will minimize the impaired healing, including pressure ulcers.

Polycystic Ovarian Syndrome (PCOS)

The use of Touchi Extract will help manage the post prandial glucose excursion and minimize the complications of this part of Polycystic Ovarian Syndrome, including infertility.

The use of Touchi Extract will help manage the post prandial glucose excursion, therefore modulating plasma insulin spikes, and minimize the endothelial dysfunction leading to erectile dysfunction. In addition, the combination of Touchi Extract with flavanols (epicatechin and catechin compounds from cocoa, wine, green tea, . . . ) may improve endothelial function by improving glycemic control and vasodilation.

The illustrative aspects of the present invention are designed to solve the problems herein described and other problems not discussed, which are discoverable by a skilled artisan.

DETAILED DESCRIPTION

As used throughout, ranges are used as a shorthand for describing each and every value that is within the range. Any value within the range can be selected as the terminus of the range. When used, the phrase "at least one of" refers to the selection of any one member individually or any combination of the members. The conjunction "and" or "or" can be used in the list of members, but the "at least one of" phrase is the controlling language. For example, at least one of A, B, and C is shorthand for A alone, B alone, C alone, A and B, B and C, A and C, or A and B and C.

All values contained throughout this application, including the claims are deemed to be approximate, whether or not the term "about" is used, unless specifically stated as exact.

The use of the term Touchi Extract (TE) shall be interpreted to mean any α-glucosidase inhibitor that would exhibit the same property in a nutritional composition or dietary regime.

The use of the term α-glucosidase inhibitor shall be interpreted to include Touchi Extract in all instances.

A dietary regimen includes, but is not limited to, a combination of food and/or drink items that fall into certain parameters (i.e. food and/or drink items that when taken together, contain a ratio of fat to protein of 1:1).

The term "mammal" includes, but is not limited to rodents, aquatic mammals, domestic animals such as dogs and cats, farm animals such as sheep, pigs, cows, and horses, and humans. Wherein the term mammal is used, it is contemplated that it also applies to other animals that are capable of the effect exhibited or intended to be exhibited, by the mammal.

Diabetes as used herein refers to states of physiologic function that fall along a continuum from euglycemic and normal insulin production and function to insulin dependency and pancreatic exhaustion, including, but not limited to: impaired glucose tolerance, insulin resistance, decreased insulin sensitivity, insulin dependence, including type 1 and type 2 Diabetes Mellitus.

Co-morbities of diabetes include, but are not limited to: cardiovascular disease, dyslipidemia, retinopathies, changes in collagen tissue, inflammation, and insulin resistance.

The present invention relates to a method of use, composition or dietary regimen containing α-glucosidase inhibitors, and more specifically Touchi Extract.

α-Glucosidase Inhibitors And Touchi Extract

Touchi Extract (TE) and other α-glucosidase inhibitors, due to their ability to inhibit carbohydrate breakdown, it is believed will act to increase the plasma concentration of glucagon-like peptide-1 (GLP-1) and glucagon-like peptide-2 (GLP-2).

GLP-1 is a hormone that is secreted from the endocrine L cells located in the distal small intestine and colon. GLP-1 acts to stimulate glucose-dependent insulin secretion, and beta-cell proliferation and neogenesis. GLP-1 is secreted in response to nutritional, hormonal and neural stimulation, with the primary stimulus being enteral nutrition. Touchi Extract is a natural α-glucosidase inhibitor that inhibits the breakdown of carbohydrates, prolonging the time carbohydrates are present in the intestine. Therefore, a greater amount of carbohydrates may reach the distal small intestine and interact with the L cells to stimulate GLP-1 secretion. It is believed that when glucose reaches the distal small intestine it may be fermented producing short-chain fatty acids that trigger the production and secretion of GLP-1 and GLP-2, and/or the sodium dependent transport of glucose across the brush border membrane of the L cell can trigger the secretion of GLP-1 and GLP-2. The increased plasma concentration of GLP-1 will improve glycemic control in addition to the effect from Touchi Extract in delaying the appearance of glucose in the blood.

GLP-2 is a hormone that is secreted from the endocrine L cells located in the distal small intestine and colon. GLP-2 acts to enhance intestinal structure and function by improving crypt-villus architecture and increasing enzyme and transporter activities. GLP-2 is secreted in response to nutritional, hormonal and neural stimulation, with the primary stimulus being enteral nutrition. Touchi Extract is a natural α-glucosidase inhibitor that inhibits the breakdown of carbohydrates, prolonging the time carbohydrates are present in the intestine. Therefore, a greater amount of carbohydrates may reach the distal small intestine and interact with the L cells to stimulate GLP-2 secretion. The increased plasma concentration of GLP-2 will improve intestinal structure and function and reduce intestinal inflammation.

Diabetes/Microvascular Complications (Kidney/Eye/Nerve)

An estimated 175 million people suffer from type 2 diabetes around the world. Diabetes is the fourth leading case of death worldwide, and complications associated with diabetes include blindness, amputations, kidney failure, heart attack and nerve damage. These complications are related to hyperglycemia, defined as elevated concentrations of blood glucose. Hyperglycemia and hyperinsulinemia causes damage to the microvascular, resulting in endothelial dysfunction and potential blindness, kidney failure and nerve damage.

Diabetic nephropathy occurs in 20-40% of individuals with diabetes, with ~43,000 people with diabetes begin treatment for kidney failure each year. Hyperglycemia is an independent risk factor for the incidence and progression of retinopathy. Neuropathy may develop very early in individuals with type 2 diabetes. The progression of diabetic nephropathy, retinopathy and neuropathy can be prevented by tight glycemic and blood pressure control.

In addition, the combination of Touchi Extract and/or other α-glucosidase inhibitors with flavanols (i.e. epicatechin and catechin compounds from cocoa, wine, green tea) may improve endothelial function by improving glycemic control and vasodilation. This combination may have a significant effect on improving the delay in the progression of the microvascular complications associated with diabetes.

Correlation Between Diabetes and Risk Factors for Cardiovascular Disease

Diabetes and cardiovascular disease (CVD) and/or coronary heart disease (CHD) share a number of risk factors. For example, individuals with high blood pressure (i.e., >140/90 mmHg), a known CVD risk factor, are at a greater risk for developing type 2 diabetes than are individuals having normal blood pressure. Similarly, individuals with high density lipoprotein cholesterol (HDLC) concentrations of 35 mg/dL or less or triglyceride (TG) concentrations of 250 mg/dL or more, both known risk factors for CVD, are also at an increased risk for developing Type 2 diabetes.

In addition, diabetes itself may be considered a risk factor for CVD, as it has been shown that persons with type 2 diabetes have a high incidence of death at time of acute myocardial infarction and have a relatively poor prognosis for long-term survival after myocardial infarction. The data above suggest, therefore, that it is advisable to treat an individual with diabetes as though he or she was at increased risk for CVD, even if the individual does not have other CVD risk factors.

Insulin Resistance

Insulin resistance is a generalized metabolic disorder, in which the body cannot use insulin efficiently. Insulin resistance occurs when the normal amount of insulin secreted by the pancreas is not able to unlock the door to cells and thus blood glucose concentrations increase while the cells are deprived of glucose (energy). To maintain a normal blood glucose and energy supply to the cells, the pancreas secretes additional insulin. When the body cells resist or do not respond to even high concentrations of insulin, glucose builds up in the blood resulting in high glucose or type 2 diabetes. Touchi Extract and/or other α-glucosidase inhibitors, inhibits the breakdown of carbohydrates, thus prolonging the time carbohydrates are present in the intestine and thereby delaying the post-prandial rise in blood glucose concentrations. This slower increase in post-prandial blood glucose concentrations can thus slow/delay the beta-cell secretion of insulin and thus minimize the exposure of the body cells to high concentrations of insulin, thus contributing to improving insulin sensitivity and decreasing insulin resistance.

Obesity

Due to its ability to inhibit carbohydrate breakdown, it is proposed that Touchi Extract and/or other α-glucosidase inhibitors will act to increase the plasma concentration of GLP-1 and GLP-2 as described above. The increased plasma concentration of GLP-1 will improve glycemic control, improve satiety and delay gastric emptying further improving satiety in addition to the effect from Touchi Extract in delaying the appearance of glucose in the blood. In addition, GLP-1 concentrations are reported to be reduced in obese individuals. Therefore, the additional Touchi Extract and/or other α-glucosidase inhibitors to weight loss supplements or other medical food products, the levels of GLP-1 could be increased and returned to normal levels.

Metabolic Syndrome/Syndrome X

Touchi Extract and/or other α-glucosidase inhibitors, inhibit the breakdown of carbohydrates, thus prolonging the time carbohydrates are present in the intestine and thereby delaying the post-prandial rise in blood glucose concentrations. This slower increase in blood glucose concentrations can play a critical role in regulating many of risk factors associated with metabolic syndrome. Lower blood glucose concentrations result in: 1. lower concentrations of insulin secretion; 2. lower rates of conversion of carbohydrates to lipids (triglycerides, VLDL-cholesterol, LDL-Cholesterol); 3. lower abdominal obesity; 4. lower insulin resistance; 5. lower blood pressure; 6. lower levels of inflammation and thrombotic factors, all of which in turn can lower the risk of chronic diseases associated with metabolic syndrome. Another potential role of Touchi Extract is its ability to stimulate GLP-1, which in turn increases satiety to aid in weight loss to weight maintenance. In addition, GLP-1 stimulates beta-cell insulin secretion and can thus help lower blood glucose concentrations, and contribute to lowered blood lipids, inflammation and thrombotic factors, blood pressure and abdominal obesity.

Heart Health/Cardiovascular Disease/Elevated Lipids

Touchi Extract and/or other α-glucosidase inhibitors, inhibits the breakdown of carbohydrates, thus prolonging the time carbohydrates are present in the intestine and thereby delaying the post-prandial rise in blood glucose concentrations. This slower increase in blood glucose concentrations can play a critical role in regulating many of the risk factors associated with metabolic syndrome. Lower blood glucose concentrations result in: 1. lower concentrations of insulin secretion; 2. lower rates of conversion of carbohydrates to lipids (triglycerides, VLDL-cholesterol, LDL-Cholesterol); 3. lower abdominal obesity; 4. lower insulin resistance; 5. lower blood pressure; 6. lower levels of inflammation and thrombotic factors, all of which in turn can lower the risk of cardiovascular disease. Another potential role of Touchi Extract and/or other α-glucosidase inhibitors is their ability to stimulate GLP-1, which in turn stimulates beta-cell insulin secretion and can thus help lower blood glucose concentrations, and contribute to lowered blood lipids, inflammation and thrombotic factors, blood pressure and abdominal obesity.

Chronic Obstructive Pulmonary Disease (COPD)

Chronic Obstructive Pulmonary Disease patients suffer from inflammation and blockage of the lungs which decreases their ability to supply oxygen to tissues. Increased resting energy expenditure is common in COPD and it is often assumed that wasting is the consequence of an imbalance between energy intake and expenditure. Cross-sectional studies have noted that subjects with diabetes have lower lung function than individuals without diabetes. In addition, both insulin-resistance and COPD are linked to inflammatory conditions and oxidative stress. Carbon dioxide is the end-product of glucose metabolism by mitochondria. As a result, COPD patients on high carbohydrate diets have to exchange more carbon dioxide from their lungs. Providing Touchi Extract and/or other α-glucosidase inhibiters will benefit the individual through reduction of hyperglycemia which leads to exacerbation of the condition caused by oxidative stress increased by blood glucose fluctuations.

Gut Integrity/Intestinal Adaptation

GLP-2 is a hormone that is secreted from the endocrine L cells located in the distal small intestine and colon. GLP-2 acts to enhance intestinal structure and function by improving crypt-villus architecture and increasing enzyme and transporter activities. GLP-2 is secreted in response to nutritional, hormonal and neural stimulation, with the primary stimulus being enteral nutrition. Touchi Extract is a natural α-glucosidase inhibitor that inhibits the breakdown of carbohydrates, prolonging the time carbohydrates are present in the intestine. Therefore, a greater amount of carbohydrates may reach the distal small intestine and interact with the L cells to stimulate GLP-2 secretion. The increased plasma concentration of GLP-2 will stimulate intestinal adaptation, improving the structure and function of the intestine, including, but not limited to, absorption of nutrients and water, secretion of protective mucins and immunoglobins, and improved barrier-protection against pathogenic bacteria.

Thus, Touchi Extract will help restore intestinal function in patients with malabsorption secondary to mucosal degeneration associated with:

cancer chemo- or radiation-therapy
Total Parenteral Nutrition (TPN)-related gut atrophy (TPN transition patients)
    acute illness-related gut dysfunction
    critically ill & septic patients
    burn & trauma patients
    surgical & medical patients
    acute pancreatitis
    intestinal inflammation in active inflammatory bowel disease Thus, Touchi Extract will help optimize intestinal function including nutrient absorption in patients following bowel resection, including those with short-bowel syndrome and post-surgery for gastrointestinal malignancy and ulcerative colitis.

Further, Touchi Extract will help restore normal intestinal function including the integrity of the gut barrier disrupted by intestinal inflammation. Patients with an inflammation-compromised gut barrier include:

acute illness-related gut dysfunction
    critically ill & septic patients
    burn & trauma patients
    surgical & medical patients
    acute pancreatitis
    intestinal inflammation in active IBD
    cancer chemo- or radiation-therapy In effect, Touchi Extract will help manage complications in these patients which include infection by pathogenic gut bacteria and diarrhea.

Specific disease states that could benefit include inflammatory bowel disease (Crohn's disease and ulcerative colitis), irritable bowel syndrome, short-bowel syndrome, malabsorption, diarrhea, constipation and gut atrophy due to transition from parenteral to enteral nutrition or radiation/chemotherapy.

GI Health/Probiotics

The addition of probiotics, preferably *Lactobacillus reuteri*, can further improve the intestinal structure and function and reduction in inflammation as well as increase the immune response previously noted with *L. reuteri*. In addition, there is the possibility of a combination of TE, probiotics and prebiotics to increase the gut structure and function as the concentration of GLP-2 would be increased, optimal amounts of butyrate would be produced through fermentation and the probiotic can have direct effects on the gut integrity and immune response to insult. Specific prebiotics could include but not be limited to fructooligosaccharides (FOS), galactooligosaccharides (GOS), inulin and partially hydrolyzed guar gum. Specific probiotics could include but not be limited to *L. reuteri, E. coli Nissle* 1917, *L. rhamnosus GG, L. casei, L. johnsonii, L. salivarius, Bifidobacteria breve, B. bifidus*, and *Sacchromyces Boulardi*.

Athletic Performance Enhancement

Both physically trained and novice athletes performing moderate exercise (cycling, jogging, swimming, etc) require a steady source of carbohydrate to maintain activity for extended periods. Commercially available sports products describe how the energy in their product is quickly metabolized and available for use. However, quickly absorbed carbohydrates increase blood sugar which in turn increases insulin activity. The natural action of insulin is to lower the blood sugar concentration through promoting entry of the glucose into the cells or by storage of the glucose. In the case of commercially available sports products, the excess blood sugar is then stored for later use, a state which may actually cause hypoglycemia that could negatively impact athletic performance. Extending the period over which carbohydrate is metabolized to glucose for absorption through the use of Touchi Extract and/or other α-glucosidase inhibitors is suggested to increase the endurance potential of athletes consuming the product.

Human Immunodeficiency Virus (HIV)

Human immunodeficiency virus infected individuals receiving highly active antiretroviral therapy (HAART) experience metabolic abnormalities including hyperlipidemia and insulin resistance. The combination of these findings has been termed the lipodystrophy syndrome. Because HAART is helping to extend the lives of HIV patients, there is a growing concern of increased cardiovascular risk in lipodystrophic individuals given the co-morbid derangements in glucose and lipid homeostasis. The use of Touchi Extract will help manage aberrant glucose and lipid metabolism through its mechanism of slowing down glucose metabolism and absorption and, thus, decrease some of the complications associated with HAART.

Cystic Fibrosis

Cystic fibrosis (CF) is characterized by thick secretions in a number of organs, including the pancreas. Most patients with CF have obstruction of the pancreatic ducts, often leading to insufficient endocrine function, such as insufficient insulin availability. This insufficiency can lead to CF-related diabetes. The use of Touchi Extract to reduce post-prandial glucose excursions could be helpful in managing CF-related diabetes by reducing the need for excess insulin secretion.

Non-alcoholic steatohepatitis (NASH)

Non-alcoholic steatohepatitis is an advanced stage of fatty liver disease in the absence of alcohol abuse. It is frequently associated with type 2 diabetes, metabolic syndrome, obesity, hyperlipidemia, and extensive small bowel resection. Insulin resistance plays a central role in the development of this type of fatty liver disease. These patients have high postprandial triglyceride levels. Touchi Extract could be used to reduce post-prandial glucose excursions therefore decreasing insulin spiking and thus be helpful in managing the type 2 diabetes that is common in NASH patients. In addition, Touchi Extract could be helpful in decreasing endogenous production of triglycerides, and therefore may play a role in helping manage the accumulation of fat in the liver, since the natural action of insulin is to lower the blood sugar concentration through entry of the glucose into the cells or by storage of the glucose, sometimes as fats, such as triglycerides.

Critical Care

Stress induced hyperglycemia is a common problem in those experiencing physiological, physical, psychiatric, traumatic, and/or iatrogenic stress. The critical care patient requires intensive glucose monitoring and insulin administration to decrease hyperglycemia due to insulin resistance. Touchi Extract enables a lower post prandial peak glucose to occur due to delayed enzyme action on carbohydrate polymers and oligosaccharides. Improved glycemic control in critical care patients has been proven to improve outcomes, for example, faster and stronger wound healing, fewer infections, and decreased complications. The use of Touchi Extract in oral nutritional supplements for critical care patients will improve glycemic control and reduce the risk of infections and other complications and improve the quality and rate of wound healing. The same rationale for tube feedings containing Touchi Extract can be assumed. The tube feeding is often disrupted due to the need to do something with the patient. Higher feed rates in the hours available for feeding will may cause hyperglycemia. Touchi Extract will reduce the degree of hyperglycemia.

Wound Healing

Elevated blood glucose concentrations, malnutrition and aging are known to delay wound healing. Patients with diabetes are a higher risk for developing peripheral neuropathy over time. This leads to a lack of sensation in the limbs, particularly the feet and lower legs. As a result of the lack of sensation in peripheral neuropathy, an irritation will often go unnoticed until a wound occurs. The healing of such wounds is difficult for a patient with diabetes The use of Touchi Extract to reduce the post prandial glucose excursion will minimize the impaired healing. The diabetic develops peripheral vascular disease with time which will cause delayed healing. They also have a less efficient conversion of arginine to NO and citrulline.

Pressure ulcers (PU) are caused by the failing of skin over bony points on malnourished and inactive persons. The skin of the elderly is typically thinner and susceptible to failure under pressure. Individuals with diabetes have an increased risk of PU and they also take longer to recover and heal after a PU has developed. The use of Touchi Extract to maintain better glucose concentrations aids in prevention and healing of PUs.

Polycystic Ovarian Syndrome (PCOS)

PCOS is a health problem that can affect a woman's menstrual cycle, fertility, hormones, insulin production and resistance, heart, blood vessels, and appearance. Specifically, PCOS patients are at high risk for type 2 diabetes. PCOS is typically managed pharmaceutically with the use of Glucophage (Metformin) and other biguanides that act by decreasing hepatic glucose production and improve insulin sensitivity. Biguanides have been shown to increase the rate of pregnancies in women that suffer from PCOS and infertility. The use of Touchi Extract will help manage the post prandial glucose excursion and minimize the complications of this part of PCOS.

Erectile dysfunction (ED)

Erectile dysfunction (ED) appears to be highly prevalent in individuals with diabetes (around 50% at 50 years of age) and more severe than in the rest of the population. Its etiology is multifactoral in this subset of patients. ED is highly correlated to multiple vascular risk factors and can be considered as a manifestation of endothelial dysfunction in general, alerting the physician to look at underlying silent coronary bed atherosclerosis. It is also dependent on the poor control of diabetes and on the presence of its chronic complications. Because of the multiple etiologies of ED in individuals with diabetes, a multifactoral approach is warranted to get an optimal response in treating such patients. The use of Touchi Extract will help manage the post prandial glucose excursion, therefore modulating plasma insulin spikes, and minimize the endothelial dysfunction leading to ED. In addition, the combination of Touchi Extract with flavanols (epicatechin and catechin compounds from cocoa, wine, green tea, . . . ) may improve endothelial function by improving glycemic control and vasodilation. This combination may have a significant effect on improving the delay in the progression of the microvascular complications associated with diabetes as well as individuals with endothelial dysfunction without diabetes.

It should be appreciated that the present invention is not limited to the specific embodiments described above, but includes variations, modifications and equivalent embodiments defined by the following claims.

What is claimed is:

1. A composition comprising at least one $\alpha$-glucosidase inhibitor and at least one flavanol, wherein the $\alpha$-glucosidase inhibitor is Touchi extract and the flavanol is at least one of an epicatechin compound and a catechin compound originating from a source selected from the group consisting of cocoa, wine, and combinations thereof, the composition further comprising a probiotic selected from the group consisting of *E. coli Nissle* 1917, *Lactobacillus johnsonii, Bifidobacterium breve, Saccharomyces boulardii*, and combinations thereof.

2. The composition of claim 1 further comprising at least one prebiotic.

3. The composition of claim 2 wherein said prebiotic is selected from the group consisting of fructooligosaccharides, galactooligosaccharides, inulin, partially hydrolyzed guar gum, and combinations thereof.

4. A dietary regime comprising at least one $\alpha$-glucosidase inhibitor and at least one flavanol, wherein the $\alpha$-glucosidase inhibitor is Touchi extract and the flavanol is at least one of an epicatechin compound and a catechin compound originating from a source selected from the group consisting of cocoa, wine, and combinations thereof, the dietary regime further comprising a probiotic selected from the group consisting of *E. coli Nissle* 1917, *Lactobacillus johnsonii, Bifidobacterium breve, Saccharomyces boulardii*, and combinations thereof.

5. A kit comprising a dietary regime selected from the group consisting of a food, a beverage, and combinations thereof of claim 4.

6. The dietary regime of claim 4 further comprising at least one prebiotic.

7. The dietary regime of claim 6 wherein said prebiotic is selected from the group consisting of fructooligosaccharides, galactooligosaccharides, inulin, partially hydrolyzed guar gum, and combinations thereof.

8. A method of treatment of a patient that can benefit from the composition as claimed in any one of claims 1, 2, and 3.

9. The method as claimed in claim 8, further comprising at least one prebiotic.

10. The method as claimed in claim 9 wherein said prebiotic is at least one of fructooligosaccharides, galactooligosaccharides, inulin and partially hydrolyzed guar gum.

11. The method as claimed in claim 8 further comprising at least one probiotic.

12. The method of treatment of a patient that can benefit from as claimed in claim 11 wherein said probiotic is at least one *L. reuteri, E. coli Nissle* 1917, *L. rhamnosus GG, L. casei, L. johnsonii, L. salivarius, bifidobacteria breve, B. bifidus*, and *sacchromyces boulardi*.

13. The method of treatment as claimed in claim 8, further comprising at least one probiotic and at least one prebiotic.

14. The method as claimed in claim 13 wherein:
(a) said prebiotic is at least one of fructooligosaccharides, galactooligosaccharides, inulin and partially hydrolyzed guar gum; and
(b) said probiotic is at least one *L. reuteri, E. coli Nissle* 1917, *L. rhamnosus GG, L. casei, L. johnsonii, L. salivarius, bifidobacteria breve, B. bifidus*, and *sacchromyces boulardi*.

15. A method as claimed in claim 8, wherein said patient has at least one of the following: Diabetes, increased insulin resistance, decreased insulin sensitivity, co-morbidities of diabetes, cardiovascular disease, coronary heart disease, could benefit from decreased lipoproteins, hyperinsulinemia, hyperlipidemia, has or at risk for fatty liver, obesity, abdominal obesity, would benefit from improve satiety, would benefit from delay gastric emptying, Metabolic Syndrome/Syndrome X, chronic obstructive pulmonary disease would benefit from improved structure and function of the intestine, malabsorption, intestinal inflammation in active inflammatory bowel disease, Crohn's disease, diarrhea, constipation, gut atrophy due to transition from parenteral nutrition, gut atrophy due to radiation therapy, gut atrophy due to radiation therapy chemotherapy, irritable bowel syndrome, benefit from enhance athletic performance, human immunodeficiency virus, cystic fibrosis, non-alcoholic steatohepatitis, is a Critical Care Patient, has a wound that is or needs assistance in healing, Polycystic Ovarian Syndrome (PCOS), Erectile Dysfunction or erectile dysfunction secondary to diabetes.

16. A method as claimed in claim 15 wherein said lipoproteins are at least one of triglycerides, very-low-density lipoprotein cholesterol and low-density lipoprotein cholesterol.

17. A method as claimed in claim 15 wherein said patient with hyperinsulinemia has at least one of: pro-inflammatory state or prothrombotic state.

18. A method as claimed in claim 15 wherein said patient has malabsoption from at least one of: cancer, chemo-therapy, radiation-therapy, total parenteral nutrition-related gut atrophy, acute illness-related gut dysfunction, being critically ill, septic, being burned, trauma, secondary to surgery, secondary to medicine, or acute pancreatitis.

19. A method as claimed in claim 15 wherein said patient has irritable bowel syndrome from at least one of: post bowel resection, short bowel syndrome, ulcerative colitis, gastrointestinal cancers, intestinal inflammation, acute illness-related gut dysfunction, being ill, being septic, being burned, trauma, secondary to surgery, secondary to medicine, acute pancreatitis, intestinal inflammation, cancer, chemo-therapy, or radiation-therapy.

20. A method as claimed in claim 15 wherein said Critical Care patient can benefit from at least one of faster and stronger wound healing, fewer infections, and decreased complications.

21. A method as claimed in claim 15 wherein said patient has a wound that is or needs assistance in healing and can benefit from at least one of: faster and stronger wound healing, fewer infections and decreased complications.

22. A method as claimed in claim 15 wherein said PCOS patient has infertility associated with the PCOS.

23. A method of administering to a patient a composition comprising administering the composition of any one of claims 1, 2 and 3.

24. A method of administering to a patient a composition as claimed in claim 23 wherein said patient is a mammal.

25. A method of administering to a patient a composition as claimed in claim 23 wherein said patient is a human.

26. A method of administering to a patient a dietary regime comprising administering the dietary regime of any one of claims 4, 6 and 7.

27. A method of administering to a patient a dietary regime as claimed in claim 26 wherein said patient is a mammal.

28. A method of administering to a patient a dietary regime as claimed in claim 26 wherein said patient is a human.

29. A method of administering to a patient a dietary regime as claimed in claim 26 wherein said dietary regime is a food or beverage or combination thereof.

\* \* \* \* \*